Dec. 23, 1941. F. D. WILLIAMS Plant Pat. 496
NECTARINE
Filed Dec. 26, 1940
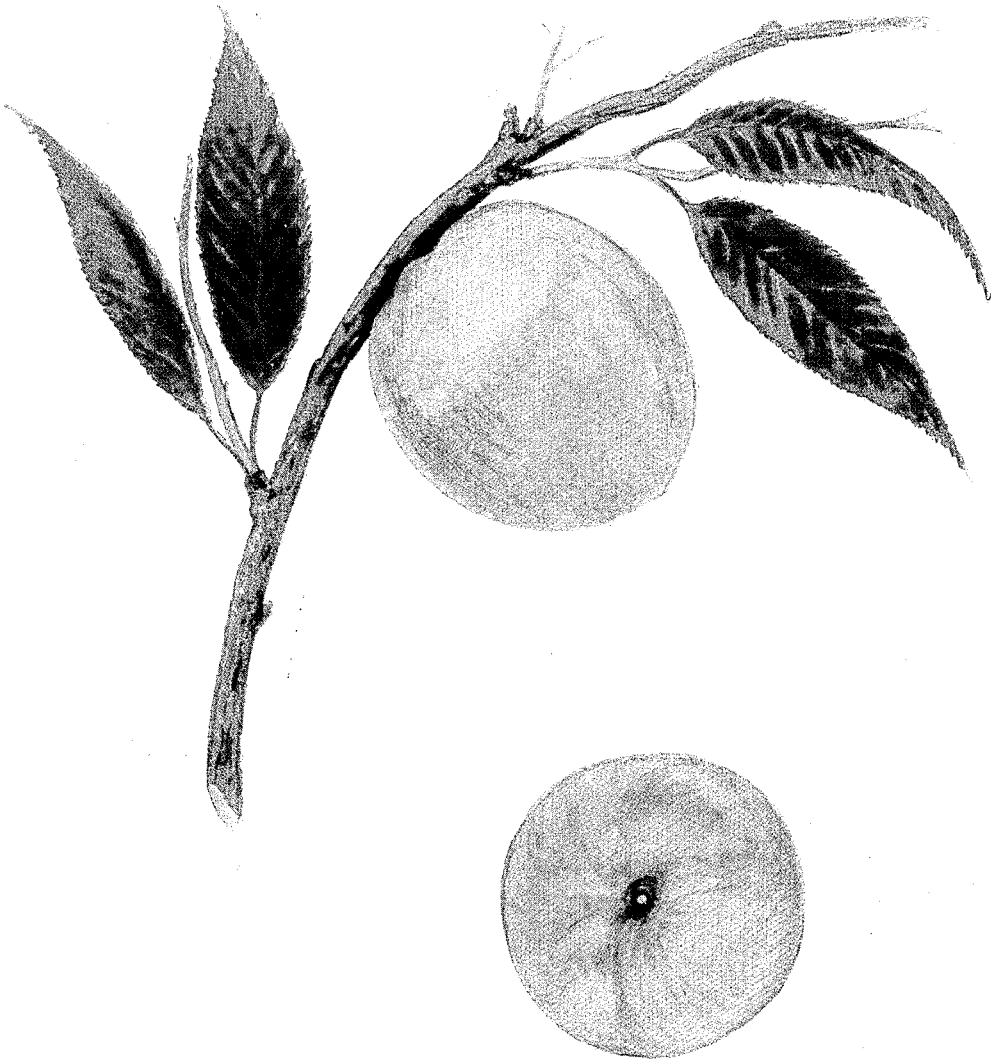
Inventor
Fred D. Williams
By Lyon & Lyon
Attorneys Patented Dec. 23, 1941

Plant Pat. 496

UNITED STATES PATENT OFFICE

496

NECTARINE

Fred D. Williams, Porterville, Calif.

Application December 26, 1940, Serial No. 371,804

1 Claim. (Cl. 47—62)

This invention relates to a new and distinct variety of nectarine having certain highly desirable characteristics, as will appear hereinafter.

The parent tree was a peach tree of the type known in the San Joaquin Valley, California, as Hutchison. The original Hutchison originated as a chance seedling and many such trees are now in existence. The name, Hutchison, has not, however, been registered.

*The Hutchison tree*

The Hutchison tree tends toward being upright, is normally vigorous and over a period of seven years has produced good average crops. The tree grows to a large size, fully as large and vigorous as the Elberta. The foliage is very abundant but is normal for peaches, both as to size and color. The leaves are serrated with regular small serrations. The tree is as resistant to common peach diseases as trees of other varieties and the commonly used spray program as used for other varieties is satisfactory. It has excellent grafting qualities and is sufficiently resistant to cold to withstand the prevailing temperatures which may occur in the San Joaquin Valley, California, peach growing area.

*The Hutchison fruit*

The Hutchison fruit is light green ground color changing to a light yellow when it ripens, with a red blush from deep to blood red on one-half to three-fourths of the fruit, with a fine speckling of red on the rest of the surface. The fruit is medium to large in size. The general form is oblique with a round apex. The base form is flat to slightly flat. The apex tip is slightly prominent and beaked.

The Hutchison fruit ripens August 10th to 20th, has a slight typical peach fragrance and a good flavor, only moderately acid. The flesh is white with a slight tending towards greenish, with a fringe of red dispersed into it immediately around the pit where it is bright red. It has smooth skin in comparison with other peaches, such as the Triumph or the Elberta, with a short fuzz and the surface is inclined to have several bumps at the base. It is a complete freestone, the stone being small to medium in size. The peel is thin to medium in thickness. As the fruit ripens, the red blush remains, greenish portions of the fruit becoming pale yellow in color.

*The nectarine tree*

The nectarine which forms the subject matter of this discovery originated as a bud-sport on a Hutchison peach tree. The original limbs and others budded onto other trees have been very productive. This nectarine originated and is reproduced upon Hutchison peach trees, described above. It is reproduced by budding. The nectarine has also been reproduced by top working on commercial peach root stock known as Shalil, which bears the plant introduction number U. S. D. A. #63,850. The nectarine trees formed by such top working upon this root stock have an exceptionally large crop for trees of the age of the Shalil trees utilized, which are at present in their third leaf.

*The nectarine fruit*

The nectarine fruit is medium to large in size, samples measured varying from 2¾ inches by 2½ inches to 2½ inches and 2¼ inches. The general form is oblique to slightly off round. It is compressed at right angles to the suture. The base form is slightly flat and the apex is mammiform. The dorsal half is slightly larger than the ventral half.

The ripening period is August 15th to 25th. The fruit has a slight nectarine fragrance and a good inviting flavor, slightly on the acid side.

The flesh is nearly white with a slight greenish tint. The flesh at the pit is a bright red with rays of red extending into the flesh approximately ⅛ to ¼ inch.

The flesh is firm and of a very fine texture, juicy but not watery. It is not mealy but rather melting.

Its shipping qualities have been found experimentally to be good.

The skin is smooth and completely devoid of fuzz. The surface is smooth with the suture not entirely regular, one carpel being higher.

It is a complete freestone, the stone being medium in size. The skin is thin but not so tender as to easily permit abrasions, yet not objectionably heavy.

In cold storage experimentally the fruit has been found to hold up satisfactorily from two to three weeks. No longer trials have been made.

No new pest or disease problems have been observed. The crops are normal and the fruit is of good marketable quality, above the average in size, and ripens during a period when other varieties of nectarines are out of season and not upon the market.

*The color of the nectarine*

Accompanying this application, in duplicate, is a full scale colored drawing showing the nectarine attached to a twig and also detached. The drawing was made with hard, nearly ripe, fruit some ten days to two weeks prior to the time when the fruit would ordinarily be picked hard ripe from the tree.

The same fruit was compared with the plates of Maerz & Paul Dictionary of Color, first edition. In this condition the fruit had a green background presenting various tints and shades of green and a predominant red, sometimes in solid spots and sometimes speckled and streaked over the fruit.

A pale Acacia green, Plate 11, K–1, page 45, formed the larger part of the background, relieved by portions and streaks of Palmleaf green, Plate 14, L–1, page 51, a brighter Lettuce green, Plate 20, L–5, page 63, light yellowish Russet green, Plate 20, K–1, page 63, and a drab Rhubarb, Plate 14, L–6, page 51. The red predominant color in its darkest shades most closely approached a Rubient red, Plate 55, L–8, page 133. A lighter Pomegranate red, Plate 6, L–3, page 35, a light Raspberry red, Plate 6, I–5, page 35, a pale Heather red, Plate 45, K–1, page 113, a darker Canyon red, Plate 7, E–6, page 37, a Garnet red, Plate 7, J–6, page 37 and a Maroon red, Plate 7, L–7, page 37, were also noted.

As noted in the drawing, the darker red portions of Rubient red are in some places solid and shade off into the various colors of red, while the green background of the paler greens is in some places almost solid and in others is speckled and streaked through the various shades of red.

As the fruit ripens, the red blush remains and the various green colors turn to a pale yellow.

I claim:

A new and distinct variety of nectarine as shown and described, characterized by the lateness of its ripening period, its size, and its redness of skin.

FRED D. WILLIAMS.